US007947015B2

(12) United States Patent
Herweck et al.

(10) Patent No.: US 7,947,015 B2
(45) Date of Patent: May 24, 2011

(54) APPLICATION OF A THERAPEUTIC SUBSTANCE TO A TISSUE LOCATION USING AN EXPANDABLE MEDICAL DEVICE

(75) Inventors: Steve A. Herweck, Nashua, NH (US); Paul Martakos, Pelham, NH (US); Geoffrey Moodie, Hudson, NH (US); Roger Labrecque, Londonderry, NH (US); Theodore Karwoski, Hollis, NH (US); Trevor Carlton, Hudson, NH (US)

(73) Assignee: Atrium Medical Corporation, Hudson, NH (US)

( * ) Notice: Subject to any disclaimer, the term of this patent is extended or adjusted under 35 U.S.C. 154(b) by 314 days.

(21) Appl. No.: 11/804,478

(22) Filed: May 18, 2007

(65) Prior Publication Data
US 2008/0015500 A1    Jan. 17, 2008

Related U.S. Application Data

(63) Continuation-in-part of application No. 10/942,764, filed on Sep. 15, 2004, now Pat. No. 7,572,245, application No. 11/804,478, which is a continuation-in-part of application No. 10/131,396, filed on Apr. 22, 2002, now Pat. No. 7,637,886, which is a continuation-in-part of application No. 09/410,329, filed on Oct. 1, 1999, now Pat. No. 6,395,208.

(60) Provisional application No. 60/503,359, filed on Sep. 15, 2003, provisional application No. 60/117,152, filed on Jan. 25, 1999.

(51) Int. Cl.
*A61M 37/00* (2006.01)

(52) U.S. Cl. .............................................. 604/103.02

(58) Field of Classification Search ............. 604/103.01, 604/103.02; 606/108
See application file for complete search history.

(56) References Cited

U.S. PATENT DOCUMENTS
4,702,252 A    10/1987  Brooks et al.
(Continued)

FOREIGN PATENT DOCUMENTS
DE           10115740 A1    10/2002
(Continued)

OTHER PUBLICATIONS

Clauβ, Wolfram, et al., "No Difference Among Modern Contrast Media's Effect on Neointimal Proliferation and Restenosis After Coronary Stenting in Pigs," *Investigative Radiology*, vol. 38(12):743-749 (2003).

(Continued)

*Primary Examiner* — Nicholas D Lucchesi
*Assistant Examiner* — Diva Ranade
(74) *Attorney, Agent, or Firm* — Morse, Barnes-Brown & Pendleton, P.C.; Sean D. Detweiler, Esq.

(57) ABSTRACT

A non-polymeric or biological coating applied to radially expandable medical delivery device provides uniform drug distribution and permeation of the coating and any therapeutic agents mixed therewith into a targeted treatment area within the body. The delivery device is expanded using the pressure of an inflation fluid. After expanding the delivery device to a pre-determined size and shape, the inflation fluid weeps through the porous surface of the delivery device. The coating releases the delivery device and floats on the inflation fluid until bonding to the tissue due to its affinity for the tissue. Once the coating bonds or affixes to the tissue, through an absorption mechanism by the tissue cells of the coating material, the coating and any therapeutics contained therein are delivered to the tissue. The fluid can contain a therapeutic agent, or can be otherwise biocompatible and/or inert.

31 Claims, 4 Drawing Sheets

U.S. PATENT DOCUMENTS

| | | | |
|---|---|---|---|
| 4,824,436 | A | 4/1989 | Wolinsky |
| 4,941,877 | A | 7/1990 | Montano, Jr. |
| 5,041,125 | A | 8/1991 | Montano, Jr. |
| 5,049,132 | A | 9/1991 | Shaffer et al. |
| 5,071,609 | A * | 12/1991 | Tu et al. ............... 264/119 |
| 5,087,244 | A | 2/1992 | Wolinsky et al. |
| 5,267,985 | A | 12/1993 | Shimada et al. |
| 5,282,785 | A | 2/1994 | Shapland et al. |
| 5,286,254 | A | 2/1994 | Shapland et al. |
| 5,295,962 | A | 3/1994 | Crocker et al. |
| 5,336,178 | A | 8/1994 | Kaplan et al. |
| 5,456,666 | A | 10/1995 | Campbell et al. |
| 5,458,568 | A | 10/1995 | Racchini et al. |
| 5,490,839 | A | 2/1996 | Wang et al. |
| 5,498,238 | A | 3/1996 | Shapland et al. |
| 5,499,971 | A | 3/1996 | Shapland et al. |
| 5,509,899 | A | 4/1996 | Fan et al. |
| 5,514,092 | A | 5/1996 | Forman et al. |
| 5,569,198 | A | 10/1996 | Racchini |
| 5,628,730 | A | 5/1997 | Shapland et al. |
| 5,634,899 | A | 6/1997 | Shapland et al. |
| 5,749,845 | A | 5/1998 | Hildebrand et al. |
| 5,800,392 | A | 9/1998 | Racchini |
| 5,807,306 | A | 9/1998 | Shapland et al. |
| 5,865,787 | A | 2/1999 | Shapland et al. |
| 5,902,266 | A | 5/1999 | Leone et al. |
| 5,947,977 | A * | 9/1999 | Slepian et al. ............... 606/108 |
| 6,048,332 | A | 4/2000 | Duffy et al. |
| 6,075,180 | A * | 6/2000 | Sharber et al. ............ 623/11.11 |
| 6,120,477 | A | 9/2000 | Campbell et al. |
| 6,146,358 | A | 11/2000 | Rowe |
| 6,206,916 | B1 | 3/2001 | Furst |
| 6,231,600 | B1 | 5/2001 | Zhong |
| 6,287,285 | B1 | 9/2001 | Michal et al. |
| 6,299,604 | B1 | 10/2001 | Ragheb et al. |
| 6,355,063 | B1 | 3/2002 | Calcote |
| 6,358,556 | B1 | 3/2002 | Ding et al. |
| 6,364,856 | B1 | 4/2002 | Ding et al. |
| 6,364,893 | B1 | 4/2002 | Sahatjian et al. |
| 6,364,903 | B2 | 4/2002 | Tseng et al. |
| 6,369,039 | B1 | 4/2002 | Palasis et al. |
| 6,451,373 | B1 | 9/2002 | Hossainy et al. |
| 6,463,323 | B1 | 10/2002 | Conrad-Vlasak et al. |
| 6,491,938 | B2 | 12/2002 | Kunz |
| 6,500,174 | B1 | 12/2002 | Maguire |
| 6,541,116 | B2 | 4/2003 | Michal et al. |
| 6,544,223 | B1 | 4/2003 | Kokish |
| 6,610,035 | B2 | 8/2003 | Yang et al. |
| 6,616,650 | B1 | 9/2003 | Rowe |
| 6,641,611 | B2 | 11/2003 | Jayaraman |
| 6,730,016 | B1 | 5/2004 | Walsh et al. |
| 6,730,064 | B2 | 5/2004 | Ragheb et al. |
| 6,758,847 | B2 | 7/2004 | Maguire |
| 6,808,536 | B2 | 10/2004 | Wright et al. |
| 6,902,522 | B1 | 6/2005 | Walsh et al. |
| 6,918,927 | B2 | 7/2005 | Bates et al. |
| 7,311,980 | B1 * | 12/2007 | Hossainy et al. ............ 428/480 |
| 2002/0082679 | A1 | 6/2002 | Sirhan et al. |
| 2003/0083740 | A1 | 5/2003 | Pathak |
| 2003/0204168 | A1 | 10/2003 | Bosma et al. |
| 2004/0013704 | A1* | 1/2004 | Kabra et al. ............... 424/427 |
| 2004/0039441 | A1 | 2/2004 | Rowland et al. |
| 2004/0137066 | A1 | 7/2004 | Jayaraman |
| 2004/0167572 | A1 | 8/2004 | Roth et al. |
| 2004/0230176 | A1 | 11/2004 | Shanahan et al. |
| 2004/0236278 | A1 | 11/2004 | Herweck et al. |
| 2005/0101522 | A1 | 5/2005 | Speck et al. |
| 2005/0106206 | A1 | 5/2005 | Herweck et al. |
| 2005/0154416 | A1 | 7/2005 | Herweck et al. |
| 2005/0159809 | A1 | 7/2005 | Hezi-Yamit et al. |
| 2005/0182485 | A1 | 8/2005 | Falotico et al. |

FOREIGN PATENT DOCUMENTS

| | | |
|---|---|---|
| EP | 1557183 A1 | 7/2005 |
| WO | WO-99/27989 A1 | 6/1999 |
| WO | WO-00/12147 A1 | 3/2000 |
| WO | WO-00/40278 A1 | 7/2000 |
| WO | WO-01/15764 A1 | 3/2001 |
| WO | WO-01/24866 A1 | 4/2001 |
| WO | WO-02/22199 A2 | 3/2002 |
| WO | WO-02/076509 A2 | 10/2002 |
| WO | WO-03/028622 A2 | 4/2003 |
| WO | WO-03/039612 A1 | 5/2003 |
| WO | WO-2004/006976 A1 | 1/2004 |
| WO | WO-2004/028582 A1 | 4/2004 |
| WO | WO-2004/028610 A2 | 4/2004 |

OTHER PUBLICATIONS

Salu, K.J., et al., "Latrunculin A inhibits smooth muscle cell proliferation adn neointimal formation in a porcine coronary stent model," *European Heart Journal*, vol. 4:143 (2002).

Scheller, Bruno, et al., "Addition of Paclitaxel to Contrast Media Prevents Restenosis After Coronary Stent Implantation," *Journal of the American College of Cardiology*, vol. 42(8):1415-1420 (2003).

Scheller, Bruno, et al., "Paclitaxel Balloon Coating, a Novel Method for Prevention and Therapy of Restenosis," *Circulation*, vol. 110:810-814 (2004).

Scheller, B., et al., "Intracoronary paclitaxel added to contrast media inhibits in-stent restenosis of porcine coronary arteries,"*European Heart Journal*, vol. 4:188 (2002).

Scheller, B., et al., "Lack of cardiotoxicity after intracoronary paclitaxel application,"*European Heart Journal*, vol. 4:295 (2002).

Scheller, B., et al., "Short-term exposure of vascular smooth muscle cells (VSMC to a contrast medium-paclitaxel formulation inhibits proliferation in vitro,"*European Heart Journal*, vol. 4:536 (2002).

Scheller, Bruno, "Paccocath ISR I trial," Euro PCR05 presentation, Nov. 22, 2010.

van der Giessen, Wim, "Glimpse into the future—Part II, Beyond the DES, A Nitric Oxide Eluting System," Euro PCR, presentation, Nov. 22, 2010.

A paper entitled, "Evaluation of the Biocompatibility and Drug Delivery Capabilities of Biological Oil Based Stent Coatings," by Li, Shengqiao of the Katholieke Universiteit Leuven, Nov. 22, 2010.

International Search Report for Application No. PCT/US04/30173, dated Mar. 8, 2006.

International Search Report for Application No. PCT/US04/30541, dated Apr. 17, 2006.

International Search Report for Application No. PCT/US2008/061419, dated Sep. 29, 2008.

* cited by examiner

APPLICATION OF A THERAPEUTIC SUBSTANCE TO A TISSUE LOCATION USING AN EXPANDABLE MEDICAL DEVICE

RELATED APPLICATIONS

This application is a continuation-in-part of, and claims the benefit of, U.S. patent application Ser. No. 10/942,764, filed Sep. 15, 2004, which claims priority to, and the benefit of, U.S. Provisional Application No. 60/503,359, filed Sep. 15, 2003, for all subject matter common to both applications. This application is also a continuation-in-part of, and claims the benefit of, U.S. patent application Ser. No. 10/131,396 filed Apr. 22, 2002, which is a continuation-in-part of now U.S. Pat. No. 6,395,208, filed Oct. 1, 1999, which claims priority to, and the benefit of, U.S. Provisional Application No. 60/117,152, filed Jan. 25, 1999. The disclosures of the above-mentioned applications and patents are hereby incorporated by reference herein in their entirety.

FIELD OF THE INVENTION

The present invention relates to therapeutic agent delivery, and more particularly to a device and/or system for delivering a therapeutic agent to a targeted tissue location within a patient to maximize the drug distribution and cellular uptake by the tissue atraumatically.

BACKGROUND OF THE INVENTION

Mechanical drug and agent delivery devices are utilized in a wide range of applications including a number of biological applications, such as catheter interventions and other implantable devices used to create a therapeutic or other biological effect within the body. Often, such delivery devices take the form of radially expandable devices used to mechanically open an occluded or narrowed blood vessel or body fluid channel or cavity. For example, inflatable non-elastomeric balloons have been utilized for treatment of body passages occluded by disease and for maintenance of the proper position of catheter-delivered medical devices, such as stents, within such body passages. With the use of both permanent and bioerodible drug carrying polymers applied directly onto the radially expandable stents to form drug eluting medical device, such devices are placed within body lumens with drugs or agents embedded therein for release of the drug or agent within the body over some pre-determined or extended period of time.

Some intervention balloon catheters are made to deliver a systemic bolus of liquid or gas that includes a drug, to a targeted tissue location within the body using an open catheter lumen or channel located at some length along the catheter shaft. Unfortunately, when such systemic delivery means are used to deliver a controlled volume of medication to a desired tissue location, a majority of the medication is lost to systemic circulation when the balloons are deflated following drug delivery and reperfusion by the body fluid or blood washes the infused deliverable away. The overall inefficiency of injectable fluids required for most small diameter catheter lumen devices lies in the dilution of the localized therapeutic agents just to pass through the length of small diameter catheter shaft. Such liquid dilution carrying mediums often prevent and limit the amount and rate at which the localized uptake of the intended therapeutic drug can penetrate local tissue after reperfusion is established upon catheter removal. Generally, most liquid formulations containing a drug or agent that is delivered to the targeted tissue location by liquid bolus does not penetrate the tissue sufficiently at the targeted tissue location to result in a significant therapeutic effect, and is consequently washed away by body fluids. This post drug delivery systemic dilution substantially diminishes the effectiveness of the drugs or agents provided through such delivery devices, and increases the likelihood of a greater systemic effect caused by the large quantity of drug or agent washed into the bloodstream. To compensate for such delivery inefficiency, the dose of drugs or agents must be volumetrically increased in anticipation that they will be principally washed away before therapeutically effecting the localized or targeted tissue area. However, because of the risk of increased systemic effects and possibly toxic overload, the volume of the drugs or agents must not exceed that which can still be considered safe for exposure by systematic dilution and subsequent systematic distribution throughout the patient's body. The drug or agent used in such an intervention delivery method must be safe enough in its diluted state to be washed away to other parts of the patient's body and not have unwanted therapeutic or otherwise detrimental effects. There is a delicate balance between making the drugs or agents sufficiently concentrated to have therapeutic characteristics at the targeted tissue location, while also being sufficiently diluted to avoid harmful effects after being washed away into the body's systemic circulation.

A further drug and agent delivery vehicle conventionally includes drug eluting stents. It is has been demonstrated that the localized concentration of drug permeation into tissue varies with the existing stent delivery vehicles, depending upon the drug load, drug dose, and release profile of such polymeric stent coatings used to carry and release the therapeutic agents after permanent stent device deployment. The drug concentrations at the struts of the stents are relatively higher than drug concentrations at areas between the struts. This can adversely affect the uniformity and localized therapeutic effect of the drug. More specifically, the drug concentration can be too high in some areas of the tissue, while the drug concentration in other areas can be inadequately efficacious. Furthermore, the distribution of the drug by a coated stent to the tissue occurs only along the struts of the stent. If the generally cylindrical shape of a stent represents a total surface area of 100%, the actual location of the struts that form the stent after expansion typically represents less than 20% of the surface area of the total cylindrical shape. Even if the surface area of the struts represented greater than 20% after radial expansion, the remaining portions of the cylindrical shape still would remain porous with a majority of large openings in the cylindrical stent geometry. The drug can only be transferred in those locations where the struts exist. Thus, with a conventional drug containing coated stent there are large sections where the drug cannot exist and cannot make direct contact with the tissue. After conventional drug eluting stent deployment, wherein a first small diameter slotted tube is inserted into the targeted organ space and expanded to a larger second diameter, the slotted tube becomes mostly open during the strut plastic deformation. Therefore, the large open sections of a deployed stent do not provide any means for delivering medication between the struts, or any means for the drug to be transferred into the tissue.

SUMMARY

There is a need for a device and corresponding method for more efficiently delivering and transferring coating material from a device to a targeted tissue location. The present invention is directed toward further solutions to address this need, in addition to having other desirable characteristics.

In accordance with aspects of the present invention, a radially expandable porous delivery device having a shaped form includes a porous body constructed of fluoropolymer material, the fluoropolymer material having a microstructure of nodes interconnected by fibrils, the nodes having an internodal distance of about 10 μm to about 30 μm and oriented to create spaces between the nodes forming channels extending from an inner surface to an outer surface of the porous delivery device through which a fluid can flow. A therapeutic coating is disposed on the outer surface of the porous delivery device having a dynamic affinity for the delivery device as well as a targeted tissue location, such that the coating remains on the device during positioning of the delivery device. An inflation fluid conduit can be disposed in the delivery device configured to supply an inflation fluid sufficient to provide an inflation fluid force to expand the porous body from a reduced diameter collapsed configuration to a pre-defined increased diameter expanded configuration. The microstructure of nodes interconnected by fibrils has a pre-determined porosity configured in part on fluid flow characteristics of the inflation fluid to cause the inflation fluid to weep through the channels at a rate substantially independent of the inflation fluid force. The therapeutic coating is configured to release from the porous body upon action of the inflation fluid weeping through the porous body.

In accordance with various example embodiments of the present invention, the porous body is configured to achieve the pre-defined increased diameter prior to the inflation fluid weeping through the microstructure of nodes interconnected by fibrils. The fluoropolymer material can be a form of polytetrafluoroethylene (PTFE). The inflation fluid weeping through the channels can have therapeutic characteristics. The pre-determined porosity can be a designated porosity for at least a portion of the porous body.

In accordance with additional example embodiments of the present invention, the inflation fluid can be at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, or contrast media. The inflation fluid can be an inert biocompatible substance, such as saline.

In accordance with various example embodiments of the present invention, weeping is achieved by the inflation fluid flowing through the microstructure of nodes interconnected by fibrils at a rate that will not injure tissue with hydraulic fluid forces. The porous delivery device can be configured to hold the inflation fluid at a pressure of about 4 atmospheres. The porous delivery device can be configured to hold the inflation fluid at a pressure of less than 6 atmospheres.

In accordance with further example embodiments of the present invention, the therapeutic coating includes fatty acids including omega-3 fatty acids. The therapeutic agent can be emulsified or suspended in the therapeutic coating. The therapeutic coating can be at least partially hydrogenated. The therapeutic coating further can include a polymeric substance, a binder, or a viscosity increasing agent to stabilize the therapeutic coating. The therapeutic coating can maintain one of a soft solid, gel, or viscous liquid consistency.

In accordance with aspects of the present invention, a method of applying a therapeutic coating to a targeted tissue location includes obtaining a collapsible porous delivery device, the device formed of a collapsible and inflatable structure with porous walls adapted to inflate to a pre-determined maximum size and shape upon introduction of an inflation fluid into the device. The method continues with applying the therapeutic coating to the delivery device, wherein the therapeutic coating has a dynamic affinity for the delivery device as well as a targeted tissue location, such that the coating remains on the device during positioning of the delivery device. The delivery device is positioned proximal to a targeted tissue location within a patient. The inflation fluid is introduced to the delivery device inflating the delivery device to the pre-determined maximum size and shape. The inflation fluid weeps through the porous walls of the delivery device and is introduced between the delivery device and the therapeutic coating, thus initiating transfer and transferring at least a substantial portion of the therapeutic coating from the delivery device to the substantial portion of the targeted tissue location. A substantial portion of the therapeutic coating contacts the targeted tissue location.

In accordance with various example embodiments of the present invention, 18. The method of claim 17, wherein a portion of the therapeutic coating permeates the targeted tissue location upon contact. The therapeutic coating can include fatty acids including omega-3 fatty acids. A therapeutic agent can be emulsified in the therapeutic coating, or suspended in the therapeutic coating. The therapeutic coating can be at least partially hydrogenated. The therapeutic coating further can include a polymeric substance, a binder, or a viscosity increasing agent to stabilize the therapeutic coating.

In accordance with further example embodiments of the present invention, upon implantation, the therapeutic coating can maintain one of a soft solid, gel, or viscous liquid consistency. The therapeutic coating can further include a solvent.

In accordance with further example embodiments of the present invention a plurality of medical devices are utilized during a procedure to apply the therapeutic coating. The inflation fluid can contain a therapeutic agent. The inflation fluid can be an inert biocompatible substance, such as saline.

In accordance with further example embodiments of the present invention, the delivery device can be inflated at a pressure of about 4 atmospheres, and can be a form of polytetrafluoroethylene (PTFE) material.

BRIEF DESCRIPTION OF THE DRAWINGS

The present invention will become better understood with reference to the following description and accompanying drawings, wherein.

DETAILED DESCRIPTION

Figure 1:
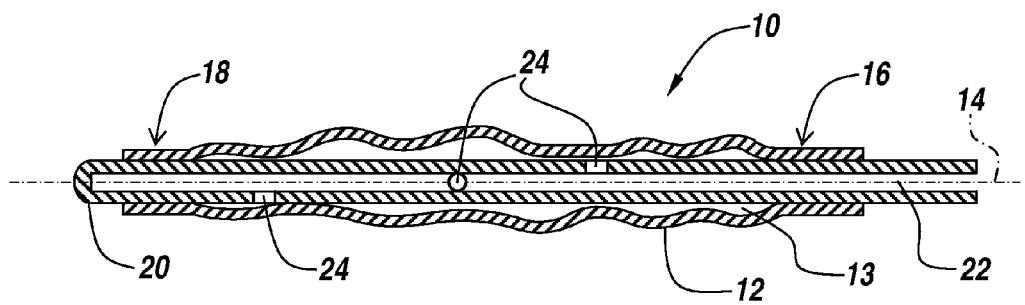
FIG. 1 is a side cross-sectional view of a radially expandable device according to the teachings of the present invention, illustrating the device in a first, reduced diameter configuration.

An illustrative embodiment of the present invention relates to use of a non-polymeric and/or biological coating that has been made to deliver a therapeutic agent or drug when applied to interventional medical devices for uniform drug distribution and more efficient cellular uptake at a targeted treatment area within the body. The present invention makes use of a sterile non-polymeric coating capable of being carried by a sterile medical device to a targeted tissue location within the body following radial expansion. Upon inflation through the radially expandable portion of the coated shaped form, the therapeutic coating begins to release and transfers off the medical device without causing trauma to the local tissue being treated. The atraumatic transfer of the drug is due in part to a biological attraction and in part to a physical transfer from the medical device to the targeted tissue location in contact with the medical device. Thus, the present invention provides a more efficient localized tissue delivery means for uniform therapeutic agent distribution and controlled bio-absorption at the targeted tissue location. The bio-absorption happens after deploying the coating by infusion means within a body cavity, organ, or tissue space. Furthermore, the biological coating transferred onto the localized tissue can be made not to induce an inflammatory response to the localized tissue or the body fluid contained within. The inflammatory response is prevented during or immediately after drug release and coating absorption by the targeted tissue or organ. For chemotherapeutic agent delivery required for molecular targeted therapeutic drug delivery, such absorbable coatings can be made to be locally toxic to the targeted treatment location or cells, tissue or body fluid. Thus, it is possible to enhance or provide a more effective localized drug kill effect without the unwanted systemic, regional or nearby biologic toxic effects to other portions of the body.

The type of radially expandable medical device to which the therapeutic substance is applied can vary, as can the method of application of the non-polymeric biological coating to the medical device, and the method of substance transfer of the non-polymeric coating from the medical device into the tissue of the body can also vary. The mode of therapeutic agent release kinetics out from the biological substance and into the tissue can also vary.

The present invention identifies a certain combination of inflation deployable coating having specific characteristics, carried to a targeted tissue location by a delivery device for which the coating has an affinity, and through the introduction of a fluid through the wall of the delivery device, unexpectedly transfers in a manner significantly more effectively than past approaches. The present invention specifically provides for the delivery of the therapeutic coating in an atraumatic manner to the vessel location.

Atraumatic means there is no dilation of the vessel, or body cavity, or other injury due to friction, shear, or other trauma inducing mechanical forces including pressure induced fluid streaming to the localized tissue. This includes the limitation that the inflation deployable coating catheter includes a porous polytetrafluoroethylene (PTFE) material shaped form that radially expands to its intended fully deployed shape and infuses fluid at low coating deployment pressures (about 4 atmospheres or less) so as to maintain some conformability and flexibility of the shaped form on the catheter within the body tissue and not injure the targeted treatment location or tissue during coating deployment due to inflation. This radial expansion means differs from non-porous and micro-porous Percutaneous Transluminal Coronary Angioplasty (PTCA) or angioplasty balloons that are designed to operate at higher pressures, such as 6 atmospheres and above.

The unique property of this novel inflation deployment coating is due to its preferred chemical formulation and material properties, which exhibits a dynamic affinity for both the porous polytetrafluoroethylene (PTFE) material forming the coating delivery vehicle, as well as the tissue at a targeted tissue location. Through the introduction of an inflation fluid through the porous shaped form wall, the coating releases uniformly from the PTFE material during radial expansion and temporarily floats on the inflation fluid surrounding the radially expandable shaped form. The released coating contacts the tissue and bonds to the tissue in contact with the expanded shaped form due to the affinity of the released coating for the targeted tissue and/or body fluid in contact with the tissue.

The inflation fluid can contain a therapeutic agent, or can be otherwise biocompatible and/or inert, such as, for example, saline. The ability of the inflation fluid to fully or partially remove the coating from the PTFE and enable the transfer of the coating to the tissue is one that has far greater effectiveness than prior attempts with inflation alone or those involved in smearing of a coating during radial expansion involved in angioplasty balloon means or other forms of localized drug delivery or elution from polymeric coating materials during radial expansion of a balloon. Following the expansion of the radially expandable device to atraumatically deploy the coating within the targeted body location, the transferred coating preferentially bonds or affixes to the tissue, through a chemical attraction or affinity of the coating. This localized coating delivery method enables the therapeutic agent to be absorbed and/or ingested more naturally, without substantial reperfusion or systemic circulation loss, protracted foreign body reaction or inflammation, and without mechanically induced trauma to the targeted or regional tissue.

FIGS. 1 through 5, illustrate example embodiments of a medical device and an application of a therapeutic coating using the medical device to a targeted tissue location within a patient, according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed in a manner still in keeping with the spirit and scope of the present invention.

The phrases "coating", "inflation deployable coating", "therapeutic drug and/or agent", "therapeutic coating", and variations thereof, are utilized interchangeably herein to indicate single or multiple therapeutic drugs within an inflation deployable coating, single or multiple therapeutic agents, or any combination of single or multiple drugs, agents, or bioactive substances that are delivered using coating deployment means. Such drugs or agents include, but are not limited to, those listed in Table 1 below herein. As such, any subtle variations of the above phrase should not be interpreted to indicate a different meaning, or to refer to a different combination of drugs or agents. The present invention is directed toward improved atraumatic delivery of a coating containing one or more therapeutic drugs and/or agents, or any combination thereof, as understood by one of ordinary skill in the art.

TABLE 1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids, NSAIDS, ibuprofen, acetaminophen, hydrocortizone acetate, hydrocortizone sodium phosphate |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus microphenonol acid, rapamycin, everolimus, tacrolimus, paclitaxel, estradiol, dexamethasone, methatrexate, cilastozol, prednisone, cyclosporine, doxorubicin, ranpirnas, troglitzon, valsarten, pemirolast, pimecrolimus, SAR 943 |
| Tissue growth stimulants | Bone morphogeneic protein, fibroblast growth factor |
| Gasses | Nitric oxide, super oxygenated O2 |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estrogen, nitric oxide |
| Second messenger targeting | Protein kinase inhibitors |
| Angiogenic | Angiopoetin, VEGF |
| Anti-Angiogenic | Endostatin |
| Inhibitation of Protein Synthesis | Halofuginone |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donative Derivatives | NCX 4016 - nitric oxide donative derivative of aspirin, snap |
| Gases | Nitric oxide, super oxygenated $O_2$ compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Chemotherapeutic Agents | Cyclosporine, doxorubicin, paclitaxel, tacrolimus, sirolimus, fludarabine, ranpirnase, zoledronic acid, imatinib mesylate (STI571/Gleevec) |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyalonic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Protein Kinase Inhibitors | PKC 412 |

Experimentally it has been discovered that mixing one or more locally efficacious therapeutic agents with a bioabsorbable oil or fat, or blend of lipid based absorbable chemistries results in a preferred therapeutic coating having an affinity to a radially expandable shaped form device and body fluid cavity or tissue space. An inflation deployable coating suitable for localized chemical affinity to wet body tissue and to radially expandable deployment devices constructed of porous PTFE material has been shown to transfer to a targeted tissue location within a patient following radial expansion of the device via low pressure inflation. An affinity and bioabsorption of a coating by the tissue at the targeted tissue location has been found to be substantially improved by use of one or more oil or fat chemical coatings capable of delivering therapeutic chemical agents. In addition, the lipophilic tissue adherence characteristic of an oil or fat has been found to reduce the likelihood that much of the therapeutic coating would be washed away by passing body fluids following reperfusion after placement of the device within the normally wet and body fluid filled targeted tissue location. Therefore, therapeutic coatings made with one or more combinations of bioabsorbable lipid, oil or fat based mixtures will preferentially adhere in place along the treatment area of the targeted tissue location, improving the bioavailability of the therapeutic agent or agents within the tissue, and thus improving the therapeutic effect to the targeted treatment area within the body.

There are several known bioabsorbable oils and fats that are appropriate for use as a coating with the present invention. One fatty acid lipid coating found to perform well with this invention was an omega 3 fatty acid, derived from either pharmaceutical grade fish oil or flax seed oil. Another lipid based fatty acid component found to function well with the present invention is a blend of tocopherols including alpha- and gamma-tocopherols. There are a number of preferred bioabsorbable lipid based chemicals, oils and fat components, some of which are listed in Table 2 below.

TABLE #2

Fish Oil
Cod-liver Oil
Squid Oil
Olive Oil
Linseed Oil
Sunflower Oil
Corn Oil
Palm/Palmnut Oil
Flax Seed Oil In addition, the mixture of therapeutic agents with such lipid based chemistries, oils or fats can include other components such as one or more therapeutic agent solvents. Various therapeutic agent solvents can serve to control or adjust the viscosity of the lipid, oil or fat coating mixture and therapeutic drug loading within the coating. Other components such as polymeric substances, binder agents, and viscosity altering agents can be added to further stabilize the therapeutic mixture, increase the drug load within the coating and/or absorption characteristics of the mixture by intended tissue target. Furthermore, the lipid, oil or fat based therapeutic coating mixture itself can be further chemically modified as an adherent viscous liquid, gel or solid coating through hydrogenation.

It has been found, surprisingly, that certain biological lipid based oils and fats temporarily adhere sufficiently strong enough to both a temporary and permanently placed indwelling catheter deployable medical devices so that most of the inflation deployable coating remains on the inserted catheter device as it is inserted into a wet, fluid filled internal body cavity, passageway, or tissue space of a patient.

Once the medical device is positioned within the body of the patient, the inflation deployable lipid based oil or fat coating, with the therapeutic agents or ingredients contained thereto, can be transferred directly onto the targeted tissue. The transfer is achieved by release of the lipid based oil or fat coating during inflation, and lipophilic affinity and bio-absorption action of the deployed lipid based oil or fat coating with the introduction of the inflation medium fluid through the porous shape form catheter device.

The chemical affinity and cellular uptake of the lipid based oil and fat now transferred onto the localized tissue in contact with the coated shaped form causes an unexpected benefit of more efficient drug distribution, absorption, permeation and delivery of the transferred coating at the targeted treatment area within the wet body tissue location. Unlike other known localized drug delivery catheter devices, providing an atraumatic means to enhance or maximize localized drug distribution, bioavailability and coating absorption to a wet or fluid filled tissue treatment without incurring high dose systemic loss of the therapeutic agent or coating, is considered to be novel.

Use of a lipid based biological oil or fat coating that has been mixed with a therapeutic agent or drug ingredient has been found to substantially improve the distribution, bioavailability and absorption of the coating and drug. Because of the chemical lipophilic affinity or attraction of the lipid based oil and fat coating, the coating deployment efficiency is high for many wet tissues within the body, as the releasable lipid based coating readily transfers from the medical device chemically intact, without need for a secondary biochemical reaction or biological reaction to remove the lipid based oil and fat coating from the medical device. The therapeutic oil and fat coating readily transfers off the medical device when applied to a radially expandable shaped form device constructed of porous PTFE and engaged with a targeted tissue location with sufficient dwell time, and with sufficient fluid introduction through the device, to allow the coated medical device to remain in close contact with the tissue for a short period of time. Once the coating deployment device becomes adequately engaged with the targeted treatment zone, the lipid based oil and/or fat coating readily transfers off of the PTFE shaped form during or after radial expansion of the medical device with the therapeutic ingredients intact, directly onto the contacted tissue with limited systemic loss or limited if any systemic therapeutic to effect to other parts of the body.

It has further been found that certain lipid based oils and fat coatings transfer off of PTFE shaped forms, having an affinity for the tissue, even in fluid filled body cavities, channels or passageways of a patient. Furthermore, the transfer occurs more completely than other known polymeric coating materials, which are also known to adhere and become absorbed over time by body tissue. More specifically, if a targeted tissue location within a body cavity requires the application of a therapeutic agent, the therapeutic agent can be applied to the targeted tissue location using a variety of different methods. The distribution, adhesion and bioavailability of the coating deployed at the targeted tissue location has been shown to be dramatically improved by mixing the therapeutic agent with a bioabsorbable lipid based oil or fat, whose lipophilic attraction to wet tissue allows for a more efficient therapeutic bioavailability and cellular uptake of the coating than most therapeutic agents delivered by inflation liquids alone in fluid filled body cavities, channels or passageways. When a therapeutic agent has been solubilized, saturated, or mixed, without polymerizing or crosslinking the therapeutic agents to themselves or the lipid based oil or fat coating, this allows all of therapeutic contents and coating to be made available for uptake, absorption, and/or permeation by the tissue. This causes a therapeutic effect by the coating deployed to the localized tissue. It has been discovered that mixing, solubilizing, and/or loading various amounts of therapeutic agents or ingredients into a lipid based oil or fat coating, suitable for adherence to a porous PTFE shaped form, without chemical cross-linking or polymerization of the lipid based oil, fat, and/or drugs or therapeutic agent ingredients to each other, the coating deployed by the catheter device obtains a sufficient localized therapeutic result without systemic effect to other areas of the same fluid filled body channel, passageway or organ. Thus, a coating consisting of a mixture of lipid based oil or fat and one or more therapeutic agents, without any chemical bonds formed between the lipid based oil or fat coating and the therapeutic agents, enhances the local therapeutic benefit of the coating deposited during atraumatic coating deployment and subsequent transfer from the radially expandable PTFE medical device.

Rather than reliance upon a chemical bonding between drug ingredient and the lipid based carrier, selected bioabsorbable lipids, fats and oils allow one or more therapeutic agents to solubilize, mix, or be held intact within the coating, to form an atraumatic therapeutic delivery complex. The therapeutic agent held within the lipid based coating without cross-linking or chemical polymerization can further be nano-particlized, dissolved, emulsified, or otherwise suspended within the lipid based oil or fat coating, enabling more than one therapeutic agents to be simultaneously absorbed by the tissue following coating deployment and absorption by the tissue.

It has been found experimentally that use of a lipid based oil or fat inflation deployable coating also dramatically reduces and or minimizes the foreign body reaction to the locally applied therapeutic agents when masked within the transferred coating. The result of this obscure coating means is a significantly reduced inflammatory reaction or condition generally caused by the introduction of most known therapeutic agents to the cells used to treat such localized tissue targets. It is known that certain oils and fats, such as omega 3 fatty acids, are not only well received by body tissue, but have exhibited their own therapeutic and bioactive benefits as well. Such lipid based oil and fat complexes also appear to reduce the otherwise common occurrence of an inflammatory reaction caused by the direct mechanical contact with the local tissue by the introduction of a mechanical delivery device, prosthesis, and/or therapeutic agent or drug coating. By mixing the therapeutic agent with the lipid based oil or fat suitable for adhesion and localized delivery by a porous PTFE shaped form, such inflammatory reactions have been observed experimentally to be greatly reduced, thus improving the outcome of the intended localized therapeutic effect within a fluid filled body space, channel or organ. Coating deployment of a lipid based coating with one or more therapeutic agents substantially improves the distribution, bioavailability, and absorption of therapeutic agents locally into the tissue made contact with the coated radially expandable inflation device. Furthermore, the inflation deployable coating improves cellular uptake of the therapeutic agent during absorption of the locally transferred therapeutic coating.

Taking into account the ability of the inflation deployable coating to perform as characterized above, the present invention includes a method and device for therapeutically treating the entire engagement area of targeted treatment zone. As an example, hollow or fluid containing organ tissues can include a coating deployment treatment zone within a blood vessel, trachea, esophagus, urethra, or prostate lumen, and/or any engagement to a hollow tissue location within the body. The localized treatment method involves engaging a transferable coating consisting of at least one lipid, oil or fat coating that is combined with one or more therapeutic agents which are engaged to a targeted treatment zone within the body by catheter intervention steps or device deployment methods used in radial expansion of the medical device by intervention techniques known in the art. In addition, this indwelling localized therapeutic treatment device applies more generally to medical device intervention procedures within fluid filled or hollow body cavities, channels or organs, and the local application of the therapeutic inflation coating to a controlled targeted treatment area during such intervention procedures.

Figure 2:
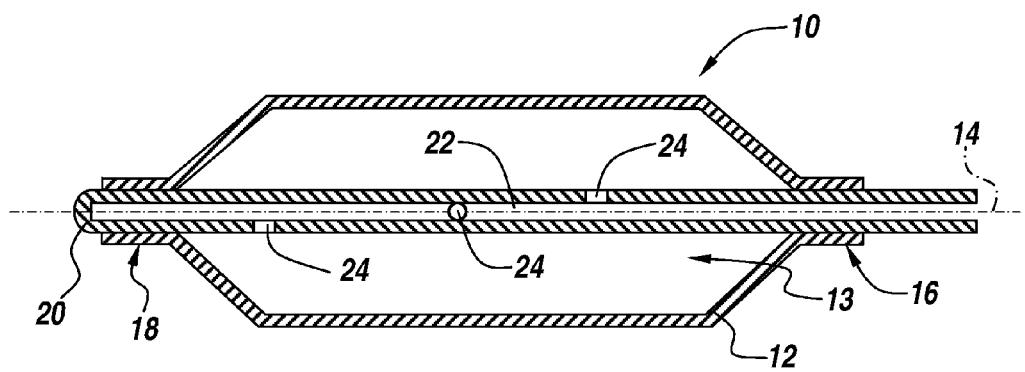
FIG. 2 is a side cross-sectional view of the radially expandable device of FIG. 1, illustrating the device in a second, increased diameter configuration.

A radially expandable device 10 having a shaped form, such as porous body 12 constructed of a generally inelastic, porous fluoropolymer material is illustrated in FIGS. 1 and 2 in accordance with the present invention. The porous body 12 of the radially expandable shaped form device 10 is deployable upon application of an expansion force from a first, reduced diameter configuration, illustrated in FIG. 1, to a second, increased diameter configuration, illustrated in FIG. 2. The fluoropolymer has a pre-defined size and shape in the second, increased diameter configuration. The porous body 12 can be dependably and predictably expanded to the pre-defined, fixed maximum diameter and to the pre-defined shape independent of the expansion force used to expand the device. That is, the porous body 12 will not expand beyond the pre-defined or pre-determined shape and outside geometry of the coated device even if the inflation pressure is increased. Said differently, the porous body 12 does not continuously expand with the continued provision of inflation fluid and inflation pressure. The porous body 12 inflates to its pre-defined or pre-determined shape upon introduction of a sufficient inflation force or fluid. Once the pre-defined or pre-determined shape is achieved, should additional inflation fluid or pressure be supplied, the porous body 12 will maintain its shape until and unless the pressure is so great as to be beyond the design limits of the device (which at some point could result in rupture of the porous body 12).

Referring specifically to FIG. 2, the porous body 12 of the radially expandable shaped form device 10 of the present invention can be, for selected narrow channel applications, preferably generally tubular in shape when expanded, although other cross-sections, such as rectangular, oval, elliptical, or polygonal, can be also be utilized with this inflation coating deployment system. The cross-section of the porous body 12 is preferably continuous and uniform along the length of the body. However, in alternative embodiments, the cross-section can vary in size and/or shape along the length of the body. FIG. 1 illustrates the porous body 12 relaxed in the first, reduced diameter configuration. The porous body 12 has a central lumen 13 extending along a longitudinal axis 14 between a first end 16 and second end 18.

An inflation mechanism in the form of an elongated hollow, porous tube 20 is shown positioned within the central lumen 13 to provide a radial deployment or expansion force to the porous body 12. The radial deployment force effects radial expansion of the porous body 12 from the first configuration to the second increased diameter configuration illustrated in FIG. 2. The first end 16 and the second end 18 are connected in sealing relationship to the outer surface of the hollow, porous tube 20. The first and second ends 16 and 18 can be thermally bonded, bonded by means of an adhesive, or attached by other mechanical sealing means suitable for inhibiting fluid leakage from the first and second ends 16 and 18 between the walls of the porous body 12 and the porous tube 20.

The hollow, porous tube 20 includes an internal, longitudinally extending lumen 22 and a number of catheter shaft channels 24 that provide for fluid communication between the exterior of the porous tube 20 and the lumen 22. The porous tube 20 can be coupled to an inflation fluid source (not shown) to selectively provide a biocompatible inflation fluid, such as saline, to the central lumen 13 of the porous body 12 through the lumen 22 and catheter shaft channels 24. As such, the porous tube 20 serves as an inflation fluid conduit. The inflation pressure from the fluid applied to the catheter device provides a radial expansion force on the porous body 12 to radially expand to the second, increased diameter configuration. Because the porous body 12 is constructed from a generally inelastic material at the prescribed inflation pressures, uncoupling the porous tube 20 from the fluid source or otherwise substantially reducing the fluid pressure within the central lumen 13 of the porous body 12, does not generally result in the porous body 12 returning to the first, reduced diameter configuration. However, the porous body 12 will collapse under its own weight to a reduced diameter after lowering and or removing the inflation fluid pressure to the device. Application of negative pressure, from, for example, a vacuum induced by the withdrawal of a syringe barrel in direct communication with the fluid connection of the device, can be used to more completely deflate the porous body 12 to near its initial reduced diameter configuration.

Figure 3:
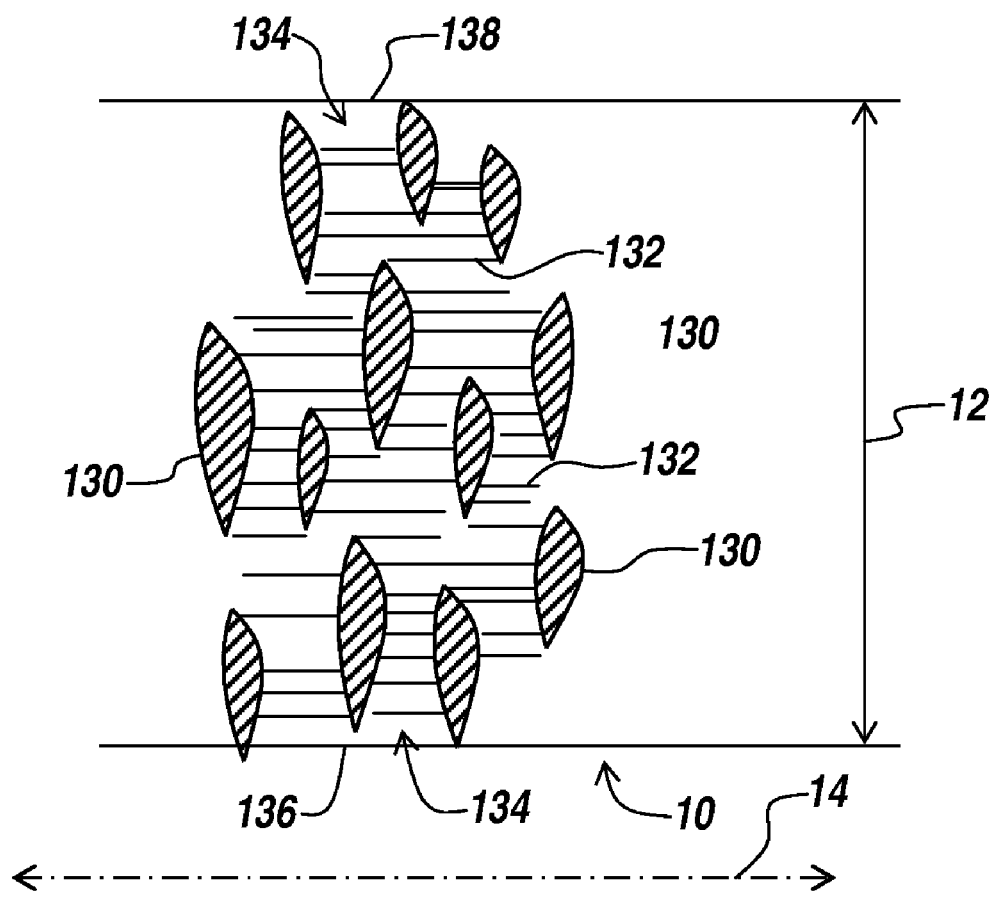
FIG. 3 is a schematic representation of the microstructure of a section of the wall of the radially expandable device of the present invention.

FIG. 3 is a schematic representation of the microstructure of the porous body 12 of the radially expandable shape form device 10. For purposes of description, the microstructure of the wall of the porous body 12 has been exaggerated. Accordingly, while the dimensions of the microstructure are enlarged, the general character of the illustrated microstructure is representative of the porous node and fibril microstructure prevailing within the wall of the porous body 12.

The microstructure of the wall of the porous body 12 is characterized by nodes 130 interconnected by fibrils or filaments 132. The nodes 130 are generally oriented perpendicular to the longitudinal axis 14 of the porous body 12. This microstructure of nodes 130 interconnected by fibrils 132 provides a porous microstructure having microfibrillar spaces which define channels or through-pores 134 extending entirely from the inner wall surface 136 to the outer wall surface 138 of the porous body 12. The through-pores 134 are perpendicularly oriented (relative to the longitudinal axis 14), internodal spaces that traverse from the inner wall surface 136 to the outer wall surface 138. The size and geometry of the through-pores 134 can be altered through the chemical preparation, formulation, extrusion and or material stretching and sintering process, as described in detail in Applicants' U.S. Pat. No. 6,955,661, filed on Oct. 1, 1999, which is incorporated herein by reference. The size and geometry of the through-pores 134 can also be altered to yield a radially expandable microstructure that consists of nodes and fibrils that can result in shaped form. The shaped form can be made selectively impermeable, semi-impermeable, or permeable by various inflation liquid viscosities, various inflation pressures or any combinations of liquid inflation viscosities and inflation pressures.

The size and geometry of the through-pores 134 can be altered to form different rates of inflation volumes, coating release rates and radial expansion fill rates within a body space or organ to effectively deliver the therapeutic coating atraumatically. For example, by twisting or rotating the porous body 12 during the extrusion, stretching, sintering and shape forming process during manufacturing, the porous channels can be oriented at an angle to an axis perpendicular to the longitudinal axis 14 of the porous body 12. As one example, the controlled porosity of the radially expandable shaped form device 10 results from the process of extrusion, followed by stretching and sintering of the polymer in its intended fully expandable diameter to lock-in the maximum diameter of the porous structure by permanent fixation of the polymeric nodes and fibril formed through-pores 134.

In accordance with one embodiment, the porous body 12, and the resultant radially expandable shaped form device 10, has a fine nodal structure that is uniform throughout the cross-section and length of the porous body 12. The uniform fine nodal structure provides the radially expandable shaped form device 10 with improved expansion characteristics as the expandable device dependably and predictably expands to the second diameter. The spacing between the nodes 130, referred to as the internodal distance (the intermodal distance is measured at each surface and across the cross-section of the balloon), and the spacing between the fibrils 132, referred to as the interfibril distance, can be in the range of 10 μm-30 μm. The interfibril distance can alternatively be in the range of 1 μm-5 μm. Moreover, the internodal distance and the interfibril distance in the preferred embodiment can be uniform throughout the length and the cross-section of the porous body 12. The uniform nodal structure can be created by forming the billet with a uniform lubricant level throughout its cross-section and length. Stretching the tubular extrudate at higher stretch rates, for example at rates greater than 1 in/s, yields in fine nodal structure. Preferably, the extrudate is stretched at a rate of approximately 10 in/s or greater. The nodal structure can also be non-uniform, by varying the location and amount of lubrication and stretching processes.

In the instance of the fluid inflating the porous body 12 of the radially expandable shaped form device 10, the inflation fluid can pass through the porous body 12 in a controlled weeping manner without jet effects to local tissue, and therefore be infused directly at a tissue target location in the patient body without mechanical trauma, injury or disruption to the underlying target tissue or therapeutic treatment area. For example, the flow rates can range from a low of about 0.5 ml/min for a 1×20 mm balloon at 1 atm with a solution viscosity of 9 cps to about 300 ml/min for a 7×10 mm balloon at 1 cps. However, one of ordinary skill in the art will appreciate that different variables, such as viscosity of the fluid, pressure of the fluid, area of the porous balloon, and the like, will have an effect on the flow rates through the balloon. The primary consideration is the avoidance of jetting or high pressure fluid emissions out of the balloon, and instead the preferred approach is a weeping action. Thus, the porous body 12 is configured in part based on fluid flow characteristics of the inflation fluid to cause the inflation fluid to weep through the channels at a rate substantially independent of the inflation fluid force.

The inflation fluid, in such an instance, can preferentially contain one or more drugs having therapeutic properties for medically treating the affected target location. Furthermore, in the instance of the radially expandable shaped form device 10 having a coating containing one or more therapeutic agents, the inflation fluid can disengage the temporary adherence effect of the lipid based therapeutic coating from the radially expandable shaped form device 10 and form a new layer between the radially expandable shaped form device 10 and the therapeutic coating. Thus, the radially expandable shaped form device 10 serves as a delivery device.

Figure 4A:
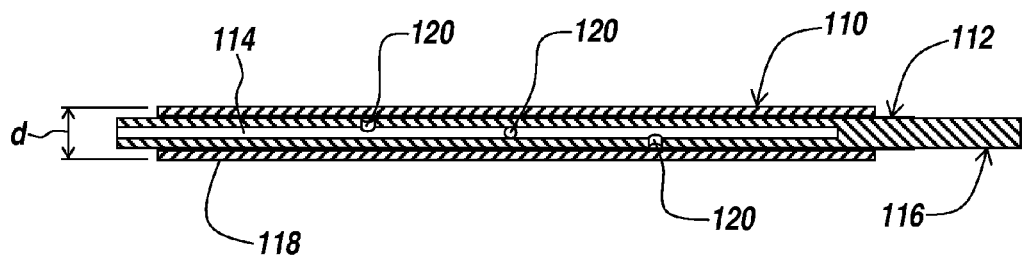
FIG. 4A is a side cross-sectional view of a the radially expandable device illustrating the radially expandable device coated with a therapeutic agent, in a deflated condition.

FIG. 4A illustrates a radially expandable shaped form device 112 having the same structure as previously described radially expandable shaped form device 10, but coated with a therapeutic coating 110, having an initial diameter d. The radially expandable shaped form device 112, such as a porous PTFE balloon, when inflated, attains a pre-determined and fixed size and shape. The radially expandable shaped form device 112 can be bonded or otherwise sealed and coupled to a rigid catheter (or hypo-tube) 116 to facilitate placement and removal of the radially expandable shaped form device 112 as described below. The catheter rigid has a central inflation lumen 118 and a plurality of catheter shaft channels 120 to provide for the delivery of an inflation fluid to inflate the radially expandable shaped form device 112.

Figure 4B:
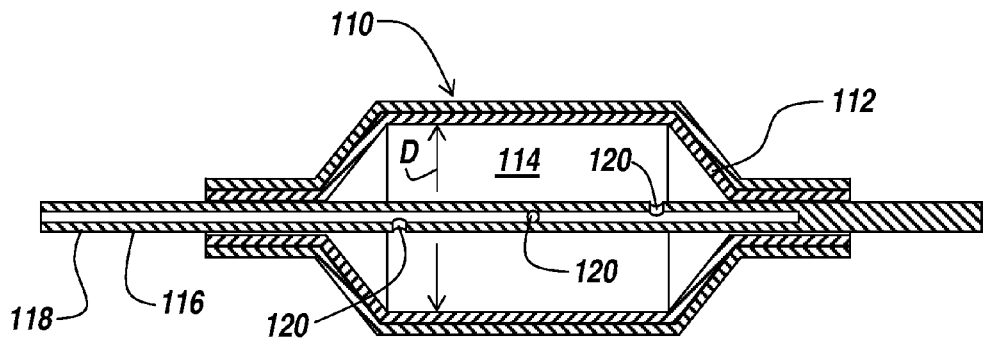
FIG. 4B is a side cross-sectional view of a the radially expandable device of FIG. 4A, illustrating the radially expandable device coated with a therapeutic agent, inflated with an inflation fluid.

Referring specifically to FIG. 4B, the radially expandable shaped form device 112 can be inflated by introducing an inflation fluid to a lumen 114 of the radially expandable shaped form device 112. The radially expandable shaped form device 112 expands until it obtains the pre-determined size and shape. The radially expandable shaped form device 112 shown in FIG. 4B is radially expanded from the initial diameter d (FIG. 4A) to an increased fixed diameter D.

Figure 4C:
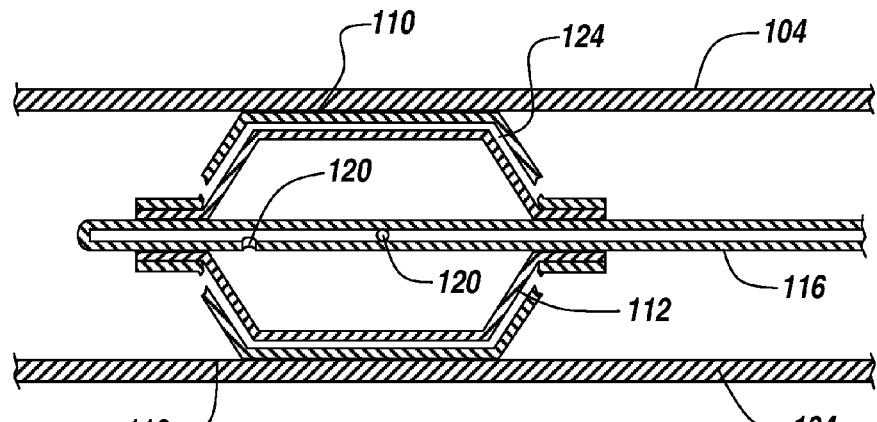
FIG. 4C is a side cross-sectional view of a the radially expandable device of FIG. 4B, illustrating the radially expandable device expanded within a body vessel.

As illustrated in FIG. 4C, the delivery of an inflation deployable coating containing one or more therapeutic agents in accordance with the present invention will be described. The radially expandable shaped form device 112 with the inflation deployable therapeutic coating 110, is inflated using an inflation fluid at a pressure of about 4 atmospheres, expanding the outer walls of the radially expandable shaped form device 112 against the vessel walls 104. The inflation fluid is provided in the lumen 114 of the radially expandable shaped form device 112 through the plurality of catheter shaft channels 120 of the rigid catheter 116. The inflation fluid fills the interior of the shaped form and expands the lumen 114 and the radially expandable shaped form device 112 to a pre-determined and fixed size and shape. The fixed size and shape is dimensionally selected by the operator not to be larger than the maximum cross-sectional opening between the anticipated interior dimension of the vessel wall 104. As such, when sized appropriately for intended treatment location within the body, the expansion of the radially expandable shaped form device 112 is atraumatic to the localized treatment area within the patient. The atraumatic deployment is accomplished by controlling the inflation pressure. During controlled inflation pressure deployment, the inflation fluid weeps through the outer surface of the radially expandable shaped form device 112 to create a fluid layer 124 between the outer surface of the radially expandable shaped form device 112 and the inflation deployable coating 110. Once the coating 110 releases from the radially expandable shaped form device 112 due to weeping by the inflation fluid, the coating transfers and bonds or affixes to the vessel wall 104. The bonding action is achieved through a lipophilic affinity action of the lipid based coating to the local tissue in contact with the released coating 110. The coating 110 and any therapeutics contained therein are delivered and remain locally intact to the vessel wall 104 during absorption of the transferred coating 110. The radially expandable shaped form device 112 is then deflated and the rigid catheter 116 is removed from the treatment location to resume body fluid flow.

The inflation deployable coating 110 containing one or more therapeutic agents is applied to at least a portion of the radially expandable shaped form device 112. Resuming the bodily fluid flow passing by the radially expandable shaped form device 112 does not dilute or wash away an efficacious amount of the therapeutic agents within the lipid based coating 110. The deployed therapeutic coating 110 additionally will transfer from the radially expandable shaped form device 112 to the targeted tissue location of the patient upon substantive contact with the radially expandable shaped form device 112. The therapeutic coating 110 remains adherent at or on the targeted tissue location. The coating 110 is then absorbed by normal lipid metabolism ingestion by the underlying tissue exposed to the coating 110. The inflation deployable therapeutic coating 110 can be applied to the radially expandable shaped form device 112 at a manufacturing stage, or applied by the operator using sterile handling techniques just prior to insertion of the radially expandable shaped form device 112 into the body.

Radially expandable devices provided by the present invention are suitable for a wide range of applications including, for example, a wide range of medical treatment applications within the body. Exemplary biological applications include use as a localized therapeutic coating delivery catheter for treatment of cancer, directed by image guidance to a remote and hard to reach location not suitable for standard systemic therapeutic delivery or radiation. Examplary biological applications further include use for treatment of a prior mechanical intervention of a vessel or fluid duct, or localized treatment of an implanted vascular graft, stent, or any indwelling permanent or temporary medical prosthesis within the body, or other type of medical implant requiring interventional therapeutic coating deployment, or for use to locally apply a therapeutic coating to a specific tissue target within the body, and to locally deliver a therapeutic coating for the treatment of any fluid filled body cavity, space, or hollow organ passage(s) such as blood vessels, the heart, spinal cord, the urinary tract, the intestinal tract, nasal cavity, peripheral vessels and or neural sheath, bone cavity, kidney ducts, and those previously intervened body spaces that have implanted vascular devices including surgical installed grafts, stents, prosthesis', or other type of medical implants. The catheter shaped form balloon can be of type with a catheter passing through a full length of the balloon, or of type with only a portion of the expandable shaped form covering the catheter shaft and located beyond the length of the catheter shaft at one end of the catheter. The radially expandable shaped form device can also be used as a sheath for covering conventional catheters and catheter balloon devices to provide localized coating deployment within the body when used in conjunction with other traditional interventional catheter devices.

Various fluoropolymer materials are additionally suitable for use in the present invention. Suitable fluoropolymer materials include, for example, expanded polytetrafluoroethylene ("ePTFE") or expanded copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. PTFE resin and various combinations of PTFE resin are often commonly employed for ePTFE medical device. Accordingly, while the radially expandable shaped form device can be manufactured from various fluoropolymer materials suitable for producing medical grade PTFE material, the material description set forth herein refers specifically to ePTFE materials. In addition, various medical grade PET polymers and or polyester nylon blends can also be utilized, depending upon the desired coating deployment properties required of the medical device.

Figure 5:
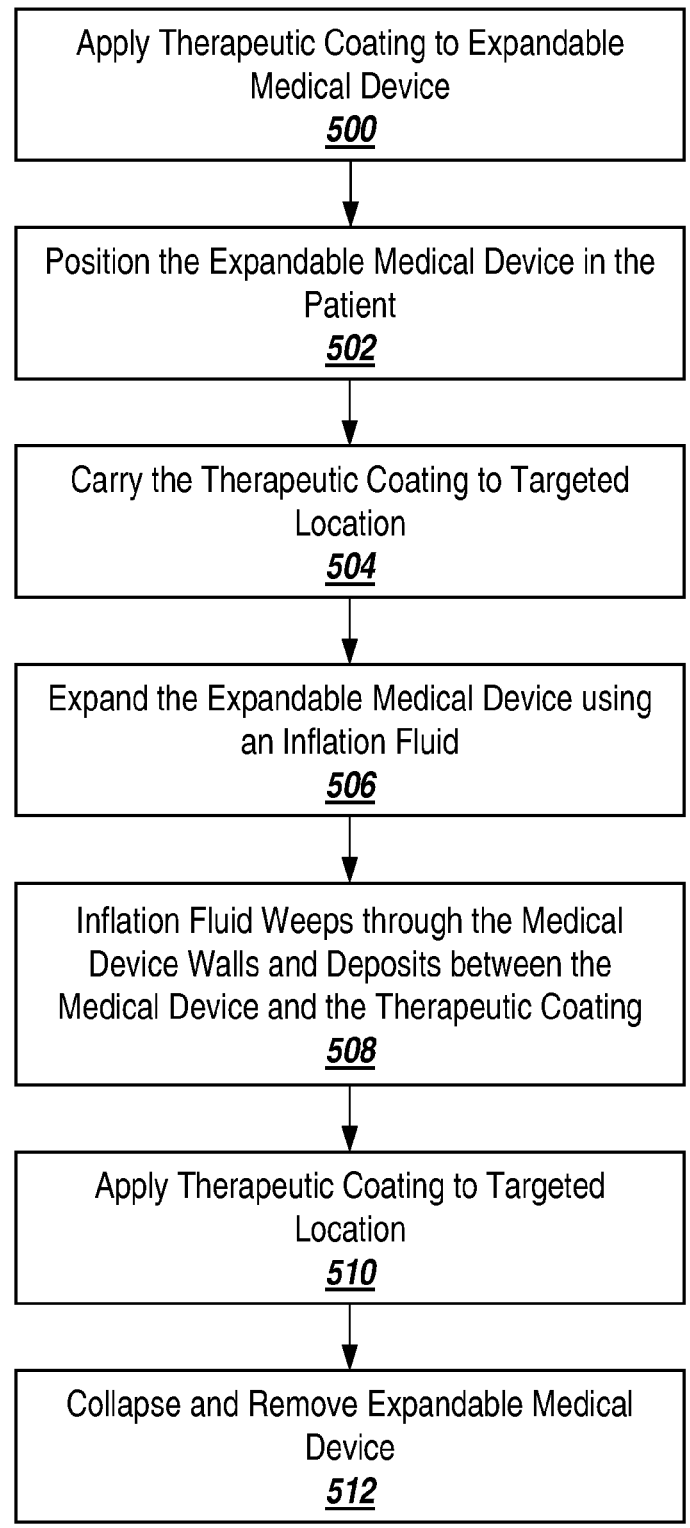
FIG. 5 is a flowchart showing a method of applying a therapeutic coating to a targeted tissue location, according to one aspect of the present invention.

In the following description of FIG. 5, a method is described for utilizing the radially expandable shaped form device 112 with the therapeutic coating 110. FIG. 5 is a flowchart illustrating one example implementation of the present invention as applied to the therapeutic agent delivery to targeted tissue locations. A therapeutic coating is applied to a radially expandable shaped form device 10 at some time prior to insertion into the vessel (step 500). The specific therapeutic coating must have an affinity for the material forming the radially expandable shaped form device 10. For example, a lipid based omega 3 coating platform consisting of pharmaceutical grade fish or flax seed oil, with or without vitamin E, can form an inflation deployable coating on a radially expandable shaped form porous PTFE catheter device.

A catheter with the radially expandable coated device is placed in a hollow organ or tissue cavity passageway (step 502). The inflation deployable therapeutic coating is carried to the treatment area by the radially expandable shaped form device 10 and delivered to a targeted tissue location when the radially expandable shaped form device 10 is expanded during fluid inflation though the porous PTFE shaped form (step 504). The medical device is expanded from a first small diameter to a second larger diameter by controlled pressure inflation through the lumen 114 of the catheter shaft and out into the interior of the coated expandable shaped form device (step 506). It should be noted that while in the larger diameter configuration, the device can be sized to adequately and temporarily occlude the vessel or body cavity during expansion of the shape form, thus blocking any blood or fluid flow during inflation deployable transfer onto the localized treatment area of the tissue. Likewise, the exterior walls of the radially expanded coated device are pressurized against the vessel walls 104 during pressure inflation. The inflation fluid weeps through the outer surface of the expandable device and forms a new fluid separating layer between the outer surface of the expandable device and the inflation deployable therapeutic coating (step 508). The therapeutic coating is thus removed from the outer surface of the expandable device allowed to float off and make contact with the localized treatment area via the lipophilic attraction of the coating and therapeutic agents to the targeted tissue during inflation and radial expansion of the device (step 510). The therapeutic coating, which has an initial stabile coating affinity for the medical device, suitable enough for coating containment and stability during mechanical placement within the treatment destination of the patient, must also have a preferred chemical attraction and affinity for the tissue. When the coating is released from the radially expandable shaped form device 10 at or along the targeted tissue location, the coating exhibits a dynamic chemical transition preference effect or modulating chemical affinity effect from one surface to another more chemically attractive surface modiety. After coating transfer from the radially expandable shaped form device 10 is completed, the device is deflated by the operator and the catheter is removed from the treatment location using regular interventional catheter techniques (step 512), while a portion of the deployed therapeutic coating remains affixed and engaged onto the targeted tissue location following removal of the radially expandable shaped form device 10.

As understood by one of ordinary skill in the art, the present invention is not limited to only one intervention procedure at the targeted tissue location. Although the locally applied inflation deployable intervention described according to FIG. 5 is principally intended for one time use, it is possible for an operator in less critical therapeutic coating delivery procedures to repeat additional coating delivery applications as necessary. For the repeated applications, the operator withdraws the device from the patient using sterile techniques and re-applies additional coating material and re-inserts the coated device back into the patient. There can be any number of different radially expandable interventional catheter procedures, each introducing a radially expandable shaped form device 10 with an inflation deployable therapeutic coating to effect a desired biological or therapeutic result at any number of targeted tissue locations within the body suitable for interventional catheter delivery. Regardless of the number of interventions performed on a targeted tissue location in accordance with the method of the present invention, the end result is that this provides for a novel atraumatic and pre-determined coating volume of a the therapeutic enabling coating. Thus, if only one intervention is performed, a larger coating dosage can be required than if the intervention requires three or more distinct coating deployment steps.

The therapeutic coating 110 can be applied to the radially expandable shaped form device 112 utilizing a number of different application methods and/or processes. For example, the therapeutic coating 110 can be dipped, whipped, painted, sprayed, or smeared onto the radially expandable shaped form device 112. The therapeutic coating 110 can be sterilized prior to clinical application or use. Alternatively, the entire sterile radially expandable shaped form device 112, or a portion thereof, can be submerged or placed into an applicator device container allowing the radially expandable shaped form device 112 to contact with the sterile therapeutic coating just prior to patient use or insertion into the body. The sterile radially expandable shaped form device 112 can be further placed into a sterile tray containing the therapeutic coating 110. Additional methods of applying the therapeutic coating 110 to the medical device can involve heating, UV curing by light or drying, or any secondary coating stabilization, or combinations thereof. One of ordinary skill in the art will appreciate that the invention is not limited by the particular method of preparing the sterile radially expandable shaped form device 112 with the sterile therapeutic coating 110. Instead, any number of different methods can be utilized to result with the therapeutic coating 110 applied to the radially expandable shaped form device 112 in a manner that promotes efficient transfer of the therapeutic coating 110 onto a targeted tissue location within a patient upon inflation and expansion of the radially expandable shaped form device 112.

The present invention relates to a plurality of combinations involving some form of therapeutic application of a therapeutic coating onto and into the targeted tissue location during use of a medical device supporting the therapeutic coating. The technique and device technology allows a multiple application step means to deliver a tissue adhering bioabsorbable therapeutic coating, one or more tissue absorbing medications or therapeutic agents, or locally toxic chemotherapeutic agents to a localized treatment area within a fluid filled body cavity, channel or organ, or preferred interventional catheter treatment means for a large internal surface area than cannot be otherwise treated systemically or treated solely by a single step local delivery means by a non-inflation coating deployment means.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the disclosed invention is reserved.

What is claimed is:

1. A radially expandable porous delivery device having a shaped form, comprising:
   a porous body constructed of fluoropolymer material, the fluoropolymer material having a microstructure of nodes interconnected by fibrils, the nodes having an internodal distance of about 10 μm to about 30 μm and oriented to create spaces between the nodes forming channels extending from an inner surface to an outer surface of the porous delivery device through which a fluid can flow;

a non-polymeric therapeutic coating disposed on the outer surface of the porous delivery device having a dynamic affinity for the delivery device as well as a targeted tissue location, such that the coating remains on the device during positioning of the delivery device;

an inflation fluid conduit disposed in the delivery device configured to supply an inflation fluid sufficient to provide an inflation fluid force to expand the porous body from a reduced diameter collapsed configuration to a pre-defined increased diameter expanded configuration;

wherein the microstructure of nodes interconnected by fibrils has a pre-determined porosity configured in part on fluid flow characteristics of the inflation fluid to cause the inflation fluid to weep through the channels at a rate substantially independent of the inflation fluid force; and wherein the therapeutic coating is configured to release from the porous body upon action of the inflation fluid weeping through the porous body.

2. The device of claim 1, wherein the porous body is configured to achieve the pre-defined increased diameter prior to the inflation fluid weeping through the microstructure of nodes interconnected by fibrils.

3. The device of claim 1, wherein the fluoropolymer material comprises polytetrafluoroethylene (PTFE).

4. The device of claim 1, wherein the inflation fluid weeping through the channels has therapeutic characteristics.

5. The device of claim 1, wherein the pre-determined porosity comprises a designated porosity for at least a portion of the porous body.

6. The device of claim 1, wherein the inflation fluid comprises at least one of antioxidants, anti-hypertensive agents, anti-inflammatory agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for inhibition of protein synthesis, anti-infective agents, agents for gene delivery, agents for local tissue perfusion, nitric oxide donating derivatives, or contrast media.

7. The device of claim 1, wherein the inflation fluid comprises an inert biocompatible substance.

8. The device of claim 1, wherein the inflation fluid comprises saline.

9. The device of claim 1, wherein weeping is achieved by the inflation fluid flowing through the microstructure of nodes interconnected by fibrils at a rate that will not injure tissue with hydraulic fluid forces.

10. The device of claim 1, wherein the porous delivery device is configured to hold the inflation fluid at a pressure of about 4 atmospheres.

11. The device of claim 1, wherein the porous delivery device is configured to hold the inflation fluid at a pressure of less than 6 atmospheres.

12. The device of claim 1, wherein the therapeutic coating comprises fatty acids including omega-3 fatty acids.

13. The device of claim 1, wherein the therapeutic agent is emulsified or suspended in the therapeutic coating.

14. The device of claim 1, wherein the therapeutic coating is at least partially hydrogenated.

15. The device of claim 1, wherein the therapeutic coating further comprises a binder or a viscosity increasing agent to stabilize the therapeutic coating.

16. The device of claim 1, wherein the therapeutic coating maintains one of a soft solid, gel, or viscous liquid consistency.

17. A method of applying a non-polymeric therapeutic coating to a targeted tissue location, comprising:

obtaining a collapsible porous delivery device, the device formed of a collapsible and inflatable structure with porous walls adapted to inflate to a pre-determined maximum size and shape upon introduction of an inflation fluid into the device;

applying the non-polymeric therapeutic coating to the delivery device, wherein the therapeutic coating has a dynamic affinity for the delivery device as well as a targeted tissue location, such that the coating remains on the device during positioning of the delivery device;

positioning the delivery device proximal to a targeted tissue location within a patient;

introducing the inflation fluid to the delivery device inflating the delivery device to the pre-determined maximum size and shape; and weeping the inflation fluid through the porous walls of the delivery device and introducing the inflation fluid between the delivery device and the therapeutic coating, thus initiating transfer and transferring at least a substantial portion of the therapeutic coating from the delivery device to the substantial portion of the targeted tissue location;

wherein the substantial portion of the therapeutic coating contacts the targeted tissue location.

18. The method of claim 17, wherein a portion of the therapeutic coating permeates the targeted tissue location upon contact.

19. The method of claim 17, wherein the therapeutic coating comprises fatty acids including omega-3 fatty acids.

20. The method of claim 17, wherein a therapeutic agent is emulsified in the therapeutic coating.

21. The method of claim 17, wherein a therapeutic agent is suspended in the therapeutic coating.

22. The method of claim 17, wherein the therapeutic coating is at least partially hydrogenated.

23. The method of claim 17, wherein the therapeutic coating further comprises a binder or a viscosity increasing agent to stabilize the therapeutic coating.

24. The method of claim 17, wherein upon implantation, the therapeutic coating maintains one of a soft solid, gel, or viscous liquid consistency.

25. The method of claim 17, wherein the therapeutic coating further comprises a solvent.

26. The method of claim 17, wherein a plurality of medical devices are utilized during a procedure to apply the therapeutic coating.

27. The method of claim 17, wherein the inflation fluid contains a therapeutic agent.

28. The method of claim 17, wherein the inflation fluid is an inert biocompatible substance.

29. The method of claim 17, wherein the inflation fluid is saline.

30. The method of claim 17, wherein the delivery device is inflated at a pressure of about 4 atmospheres.

31. The method of claim 17, wherein the delivery device is formed of polytetrafluoroethylene (PTFE) material.

* * * * *